United States Patent [19]

Arribard et al.

[11] Patent Number: 4,905,005

[45] Date of Patent: Feb. 27, 1990

[54] LOGARITHMIC CONVERTERS AND THEIR APPLICATION TO THE MEASUREMENT OF TRANSMITTED LIGHT

[75] Inventors: Herve Arribard, Montmorency; Bruno Cornut, Pau; Gilbert Passade, Bizanos; Claude Sesques, Pau, all of France

[73] Assignee: Inovelf, France

[21] Appl. No.: 189,408

[22] Filed: Apr. 27, 1988

Related U.S. Application Data

[63] Continuation of Ser. No. 102,651, Sep. 30, 1987, which is a continuation of Ser. No. 860,208, May 6, 1986, abandoned.

[30] Foreign Application Priority Data

May 6, 1985 [FR] France ................. 85 06820

[51] Int. Cl.$^4$ .................................. H03M 1/18
[52] U.S. Cl. .................... 341/139; 356/408
[58] Field of Search ............... 341/120, 139, 155; 356/408

[56] References Cited

U.S. PATENT DOCUMENTS

| | | | |
|---|---|---|---|
| 3,530,458 | 9/1970 | Willard et al. | 341/120 |
| 3,735,393 | 5/1973 | Carbrey | 341/139 |
| 3,813,609 | 5/1974 | Wilkes et al. | 341/139 |
| 4,291,895 | 9/1981 | Tsujimura | 356/408 |
| 4,366,469 | 12/1982 | Michaels et al. | 341/139 |
| 4,439,038 | 5/1984 | Mactaggart | 356/408 |
| 4,467,438 | 8/1984 | Zerlaut et al. | 356/408 |
| 4,616,210 | 10/1986 | Ferber et al. | 341/139 |
| 4,616,329 | 10/1986 | Abrams et al. | 341/120 |

OTHER PUBLICATIONS

Sheingold et al., Analog-Digital Conversion Handbook, Jun. 1972, pp. I-2,3,8,9, and 30-35.

Primary Examiner—William M. Shoop, Jr.
Assistant Examiner—Marc S. Hoff
Attorney, Agent, or Firm—Bacon & Thomas

[57] ABSTRACT

The object of the present invention is the improvement of logarithmic amplifiers and/or converters and the applications of such devices in particular to photometric analyzer apparatuses.

These amplifiers are characterized by the fact that they are linear with an amplification gain programmable by the $\mu$P computer and that they may be preceded optionally by a reference voltage system.

Application to the measurement of light transmitted by samples.

24 Claims, 3 Drawing Sheets

LOGARITHMIC CONVERTERS AND THEIR APPLICATION TO THE MEASUREMENT OF TRANSMITTED LIGHT

This is a continuation of Ser. No. 102,651, filed 9/30/87, which is a continuation of Ser. No. 860,208, filed 5/6/86, now abandoned.

The object of the present invention is the improvement of logarithmic amplifiers and/or converters and the applications of such devices, in particular to photometric analyzer apparatuses.

In such applications, as in numerous others well known from the prior art, reference is made to a variable which is detected and/or measured and which an exponential function of the value desired at the outlet, which is why logarithmic amplifiers placed downstream from the detectors are captors, are used. More and more, however, digital outputs are sought, which permit digital displays and/or access to computers and/or to other devices for the processing of digital data.

Therefore, if analog logarithmic amplifiers are used, it should theoretically be sufficient to follow them with a CA/N analog/digital converter, but this requires a very high degree of precision of the logarithmic amplifier which generally is not the case, except at a cost that is disproportionate in view of the application intended.

To illustrate the problems that may arise, referenhce may be made as an example to the measurement of the luminous transmission of a sample. If $I_O$ is the intensity of the light at the inlet of the fluid sample and I the intensity at the outlet, the Beer-Lambert law may be written as:

$$I = I_O \exp(-\epsilon t C) \qquad (1)$$

wherein $\epsilon$ is the so-called molecular extinction coefficient, t the length of the path of the light through the sample and C the concentration of the chromogen, from which $$C = -1/\epsilon t \, \text{Log}\,(I)/(I_O) \qquad (2)$$

In actual fact this equation is ideal; if reflections and losses are taken into consideration the formula becomes more complex, but always results approximately in:

$$C = A \, \text{Log}\,(I) + B \qquad (3)$$

wherein A and B are constants.

If therefore the light I transmitted is measured by means of a sensor, for example, an optoelectronic detector emitting a current i which varied linearly with I, one obtains at the outlet of the electronic assembly a signal S representing the value of C in the form of:

$$S = a \, \text{Log}\,(i) + b \qquad (4)$$

wherein a and b are constants.

With the logarithmic amplifiers of the prior art, in an application of Equation (4) it is necessary to control a and b, together with the linearity of S as a function of Log (i) which is never perfect, the more so if it is desired to convert the analog data into digital data. Drifts would appear, in particular, in time.

Furthermore, conventional analog amplifiers prevent the measurement of signals below a certain threshold and make it impossible to measure black (zero).

It must be emphasized further that when linearity is not assured exactly, not only the taking into account of the error in S becomes important, but also the error of the slope which differs from that of the straight line representing S as a function of Log (i). It is possible in effect that, within certain signal ranges, the value of S differs only slight from the ideal value or may even be equal to it, but the value of the derivative in contrast varies very differently.

It thus appears that in applications such as photometric measurements of the variation of luminous absorption, one works with signal variations and rather than the divergence of the logarithmic function itself, it is the divergence of its derivative that may become prohibitive.

It is thus the object of the present invention to provide assemblies to perform amplification, logarithmic transformation and the analog/digital conversion. While heretofore the first two operations was effected in logarithmic amplifiers and the latter in a converter, it has now been discovered that it is possible to perform linear amplification followed by analog/digital conversion and finally by the logarithmic transformation, in a digital computer, i.e. essentially in a microprocessor.

By moving the analog/digital conversion ahead of the logarithmic transformation the uncertainty of the logarithmic transformation is eliminated. It is then sufficient to insure the linearity of the transformer.

At this point, however, the problem of the cost of analog/digital converters which is closely linked to capacity, arises. Although 12 bit CA/N-s (CA/N: convertisseur analogique/numerique=analog/digital converter), capable of converting $2^{12} = 4096$ different signal levels, are currently available at reasonable prices, beyond 12 bits converters become less common and increasingly expensive. If it is required to process, for example, signals of the order of 500,000 different levels, a 19 bit converter must be used ($2^{19} = 524\,288$), which involves the aforementioned problems.

According to the invention a linear amplifier with its gain variation controlled by a microprocessor or an equivalent device is used, so as to maintain the converter receiving the signals of the amplifier below saturation.

To illustrate this condition, recalling the example of the 12 bit CA/N, while it is desired to operate with up to 19 bits, reference is made to FIG. 1 (logarithmic coordinates).

If it is current received by the amplifier from the detector and S the signal transmitted by the amplifier to the converter, ideally one should operate along the straight line AB, i.e. for i and S varying from 1 to $2^{19}$, but the straight line CD of the $2^{12}$ ordinate corresponds to the saturation of the converter. It is possible therefore to amplify between A and E only, i.e. a limitation to $2^{12}$ or 12 bits. If now upon arriving at E the gain of the amplifier is altered, it is possible to proceed for example to the point F on the straight line GH which is parallel to AB; G on the i axis corresponds to 7 bits (128); H on the saturation line CD corresponds to $2^{19}$ for i and $2^{12}$ or 12 bits for S. It is thus apparent that one may operate along AE to the saturation limit, then by lowering the gain of the amplifier proceed to F ($2^{12}$ for i, $2^5$ or 32 bits for S) and to H ($2^{19}$ for i and $2^{12}$ or 12 bits for S, i.e. within the range desired both for i and S).

However, while at E the resolution is 1/4096, at F it is 1/32, which is highly undesirable. It is possible therefore to conceive of several changes in gain and works for example along EJKLMNPQRSTUVWH.

In the case in which a signal is followed over a period of time, it is possible to travel different paths, for example to guard against variations in gain which may be detrimental, as seen in the example below.

However, even when using such a system there remains a degree of uncertainty concerning the accuracy of the different gains and therefore in certain applications controls may be useful, said controls being provided according to the invention by a self-calibration system effecting controls and corrections prior to each series of operations. It is also possible to perform them upon each change in gain.

The present invention therefore essentially relates to an assembly consisting of an amplifier with a programmable gain, optionally preceded by a voltage divider with programmable attenuation and followed by an analog/digital converter and a microprocessor controlling the gain of the amplifier and the attenuation of the optional voltage divider, with the microprocessor varying the gain of the amplifier whenever its output exceeds upwardly the saturation threshold of the converter and in the downward direction a value selected so as not to lose resolution.

In order to render more apparent the technical characteristics and the advantages of the present invention, certain examples of embodiment and application are described below, with the understanding that they are not limited relative to their mode of operation and the applications wherein they may be used. Reference is made to the figures attached hereto, which schematically show the following:

The detection and computation chain essentially comprises a detector, sensor or the like D, a linear preamplifier PA, a liner amplifier A, an analog/digital converter CA/N and a microprocessor $\mu P$.

The gain of the amplifier A is programmed by means of switches controlled elelctronically by the microprocessor $\mu P$.

In front of the amplifier A, a voltage divider functioning as an attenuator may be provided, said divider being programmed by means of switches controlled electronically by the microprocessor $\mu P$.

By means of the resistances $R_G$ it is thus possible to modify the gain of the amplifier A, i.e. (FIG. 1) to locate on one of the segments AE, JK, LM, NP, QR, ST, UF or WH or their downward extension (with the exception of AE, obviously).

Figure 1:
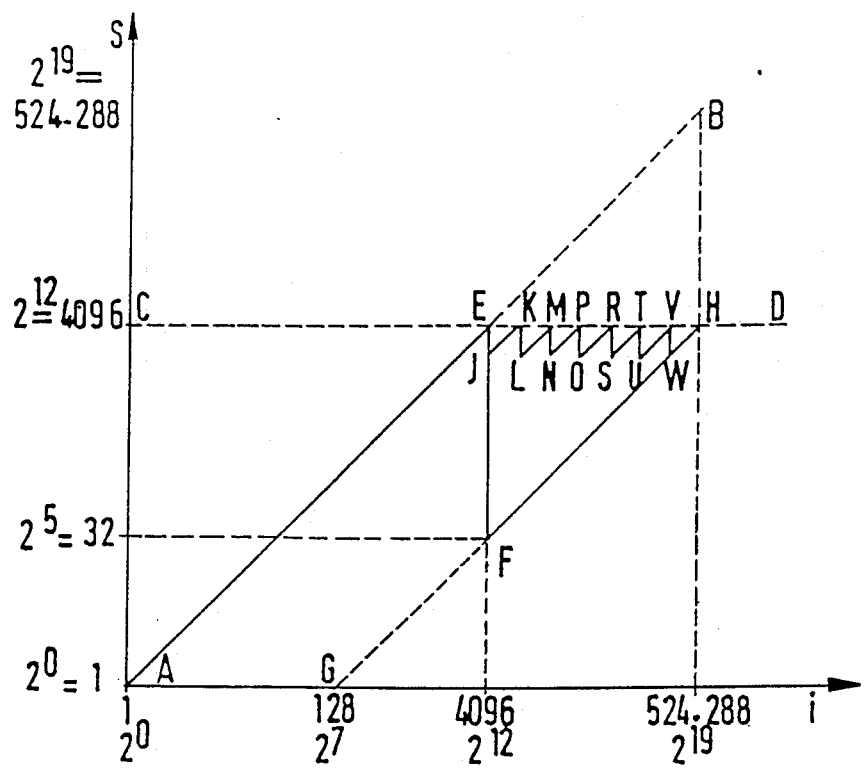
FIG. 1 is a diagram of the variations in gain as a function of the input signals.

In the measuring phase, the signals pass directly from the linear preamplifier PA to the amplifier A, the gain of which will be modified by the microprocessor $\mu P$ by means of electronic switches which select the resistance $R_G$ corresponding to different gains, so as to operate for example according to AEJKLMNPQRSTUVWH of FIG. 1, i.e. AEFH or any other combination of gain variations making it possible to remain under the saturation threshold of the converter CA/N.

Consequently, when the microprocessor receives signals deviating above the saturation threshold or below the value chosen so as not to lose resolution as indicated above, it commands a change in gain and thus a return to said threshold of said value.

The microprocessor $\mu P$, which receives the digitalized data from the converter CA/N, further performs the logarithmic transformation by using on the one hand the gain values recorded in the memory and on the other, a logarithmic computer algorithm recorded in read-only memory.

If a voltage divider is used, the values of the gain ratios are recorded in a read-write memory as they result from the operations described below. In the contrary case, these values may be recorded in a read-only memory.

In a case of an application to photometric measurements for analytical purposes, the knowledge of the ratio of gains is in effect sufficient, as the methods used, whether kinetic or final point, are based on the measurements of concentration differences at different points in time, and therefore on measurements of signal ratios at different instances (Formula (2)). Absolute self-calibration of the apparatus is possible without the use of a reference that in itself is absolute and stable in time. It is thus sufficient to measure any voltage V at different gains and to calculate the ratio between the ratio of the output signals of the amplifier A for all successive pairs of gain:

$$V_{g_i}/V_{g_{i+1}}$$

However, a single value of V may be insufficient to assure adequate measuring precision for each of the pairs of gain. Also, the programmable voltage divider makes it possible to select at the inlet of the amplifier A, $V_i$ voltages well adapted to each pair of gains.

Prior to a measuring operation, the microprocessor $\mu P$ controlling the divider $D_V$ by means of its electronic switches selects a voltage $V_i$ and measures the ratio of the output signals of the amplifier A for two successive gains, i.e.

$$V_{ig_i}/V_{ig_{i+1}}$$

which makes it possible to place into the read-write memory the gain ratio values controlled in this manner and to cause the microprocessor to perform the necessary corrections.

It should be noted further, prior to describing in detail the operation of the system, that it is possible to use not a voltage divider but one or several reference electrodes.

Figure 3:
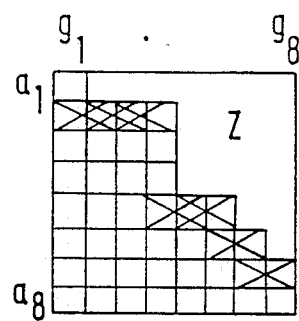
FIG. 3 is a table of two parameters; amplifier gain and attenuation of the voltage divider.

The operation will be discussed with reference to FIG. 3 which shows the different gains $g_1$ to $g_8$ of the amplifier A and the attenuations $a_1$ to $a_8$ of the voltage divider $D_V$, corresponding preferably to successive divisions of the voltage by 2, 4, 8, 16, etc.

It is noted that a zone Z of the table which would correspond to saturations must be eliminated. A broken line has been drawn here, as an example, to limit the said zone. A practical method is to measure for each attenuation $a_1 = V_i/V$ of the divider $D_V$ the signal for each gain $g_i$ of the $R_G$ circuit. Preferably, therefore, one would use two horizontally adjacent cases of the table of FIG. 1, each pair being indicated by an X to find the most favorable resolution conditions.

In a slightly different version, and if the application requires it, the dynamics of the system may be extended further by using the programmed voltage divider $D_V$ not only in the fine self-calibration of the conversion chain, but also in the course of the measurement to more or less attenuating the output signal of the preamplifier PA, if the need should arise. In such an application, the weakest signals are measured by setting the attenuation to its minimum value (the value 1, if the outlet of the preamplifier PA is connected directly to the inlet of the amplifier A) and by varying the gains of the amplifier A by acting on the circuit $R_G$, and the strongest signals are measured by setting the gain of A to its lowest value that may be obtained with $R_G$ and by varying the attenuation by acting on the divider $D_V$. Any other combination of attenuation values, by acting on $D_V$ and the gain and on $R_G$, is conceivable. If greater precision is required, the most accurate knowledge of successive attenuation factors supplied by $D_V$ is absolutely necessary. They may be obtained from the table of FIG. 3 by calculating the ratios of the values of this table contained in two vertically adjacent cases by seeking, for a given pair of successive attenuation factors, the most favorable resolution conditions.

Figure 2:
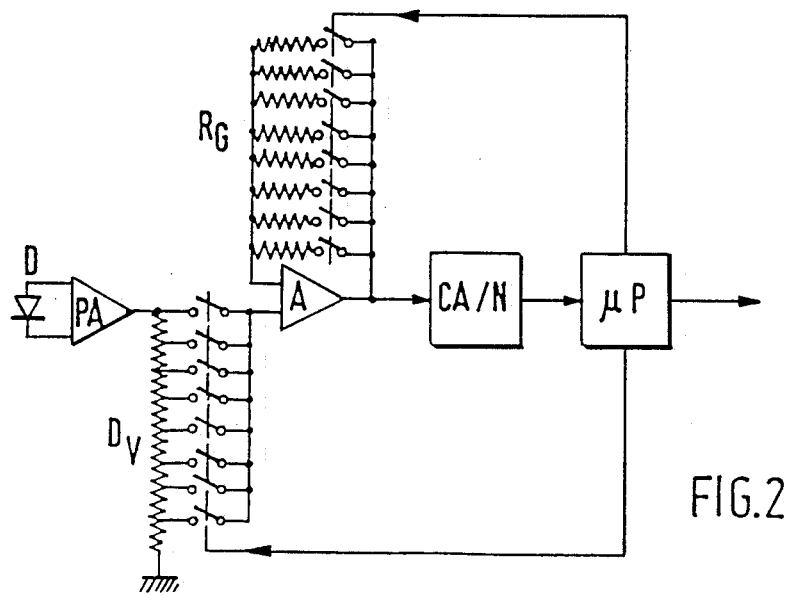
FIG. 2 is a fundamental circuit diagram according to the present invention, one mode of embodiment whereof is described in more detail in FIG. 4.
Figure 4:
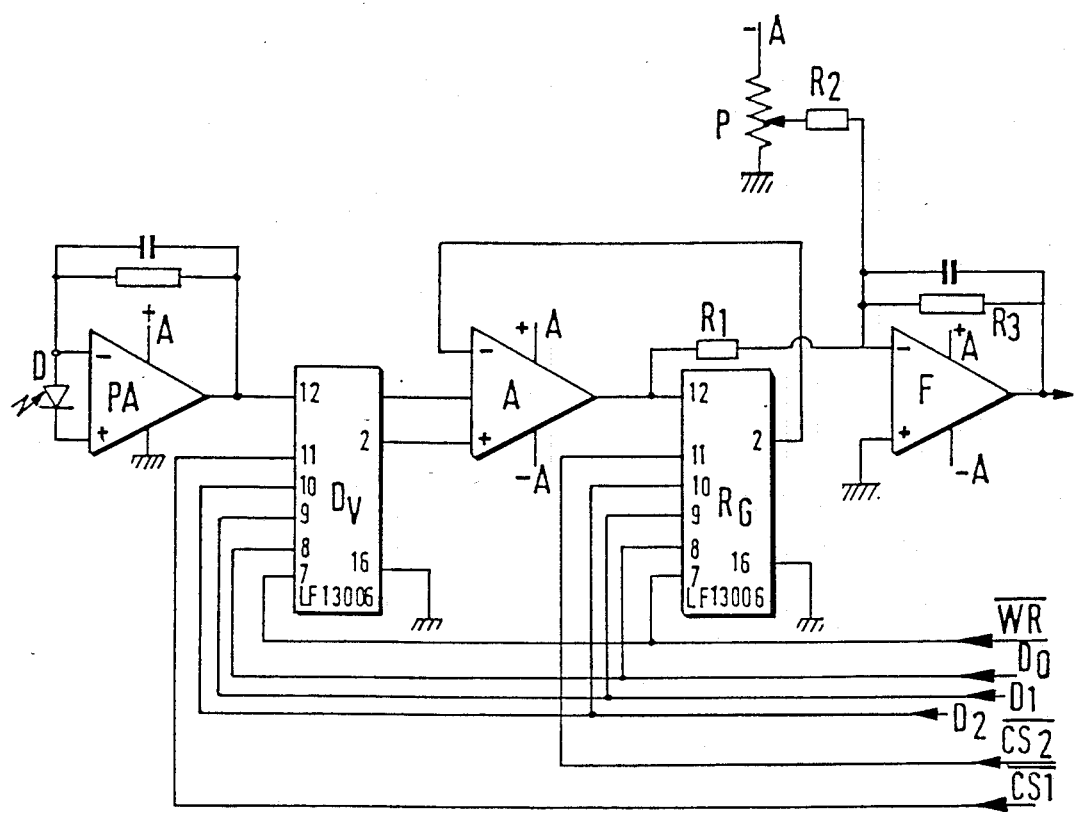
FIG. 4 is a more detailed diagram of the embodiment of the circuit in FIG. 2.

It is obvious that in view of the present state of technical development a circuit similar to that of FIG. 2 may be prepared by using conventional components and in particular integrated circuits. FIG. 4 shows a mode of embodiment illustrating the use as the voltage divider and the battery of resistances to vary the gain, two integrated LF 13006 circuits of National Semiconductor.

These circuits comprise essentially a series of resistances and it is possible to connect between them by means of 8 electronic switches controlled by a 3 bit decoder.

FIG. 4 shows under the same reference symbols the elements of FIG. 2, the two integrated circuits playing respectively the role of the voltage divider $D_V$ and the battery of resistances $R_G$ to change the gain.

The assembly may be followed by a low-pass filter F.

FIG. 4 indicates only certain lead-ins $+A$ and $-A$ and in order to simplify the drawing omits a number of conventional components or connections, which are not part of the invention.

The signals emitted by the preamplifier, which itself receives the signals of the detector D or another sensor, arrive in the circuit $D_V$ through the inlet 12. Its outlet 2 is connected with the $+$inlet of the amplifier A, the outlet of which is in turn connected with the inlet 12 of the circuit $R_G$, with the inlet 2 of the latter is connected with the $-$inlet of the amplifier A.

The outlet of the amplifier A is also connected by a resistance $R_1$ with the inlet of the filter F, the $+$inlet of which is at ground. A negative voltage is also applied through the resistance $R_2$ to the $-$inlet of the filter F, said voltage being coarsely regulated by the potentiometer P, which shifts the signals issuing from F upwards, while insuring that these signals will always be strictly positive, so that the values may be converted effectively by the analog/digital converter. In a preferred version, the resistance $R_1$, $R_2$ and $R_3$ are chosen to be equal to each other and are connected with the remaining available pins of the circuits $R_G$ and $D_V$.

The outlet of the filter F is connected with the analog/digital converter CA/N of FIG. 2, not shown in FIG. 4, which is followed by the microprocessor $\mu P$ of FIG. 2, not shown in FIG. 4.

The two integrated circuits are controlled by the microprocessor under the following conditions: their inlets 8, 9 and 10 receive the three selection bits $D_0$, $D_1$, $D_2$ of the microprocessor, with the inlets 7 receiving the WR command to consider the gain (for $R_G$) or the attenuation (for $D_V$), the selection between gain or attenuation being controlled respectively by $CS_1$ or $CS_2$. The WR, $D_0$, $D_1$, $D_2$, $CS_1$, $SC_2$ beam originates in the microprocessor $\mu P$.

The preamplifier PA may be constructed for example by means of a 3528 CM circuit of Burr-Brown, the amplifier A by means of a 547 KH and the filter F by means of an OP 07EH, both of Analog Device.

As mentioned above, the divider $D_V$ may be replaced by one or several reference voltages, if possible within a given context.

It is obvious that amplification, logarithmic and analog/digital conversion assemblies find innumerable applications in conventional voltage and/or intensity measuring devices for which they provide the advantage of self-calibration and digital output, making possible visual display, together with the ability to connect with any data processing apparatus.

Again as mentioned hereinabove, devices according to the invention find a particularly appropriate application in the solution of problems in the field of analysis by measurements of luminous transmission.

Let us consider as an example an application to biological metering involving an enzymatic reaction manifested by the appearance or disappearance of a chromogen. The object is to follow the variation in time of the concentration of the chomogen by measuring the variation of the intensity of the light transmitted over an adequate length through an optical cell in which the enzymatic reaction takes place (kinetic method or "final point" method). Formula (2) shows that a difference in the concentration of the chromogen between two points in time translates into a ratio of luminous intensities and that consequently, but using a programmable electronic device of the aforedescribed type for the measurement of gain and optionally of attenuation, a precise knowledge of grain ratios (and possibly also of attenuation factors) is necessary, rather than a knowledge of absolute values of the gains and attenuation factors.

Figure 6:
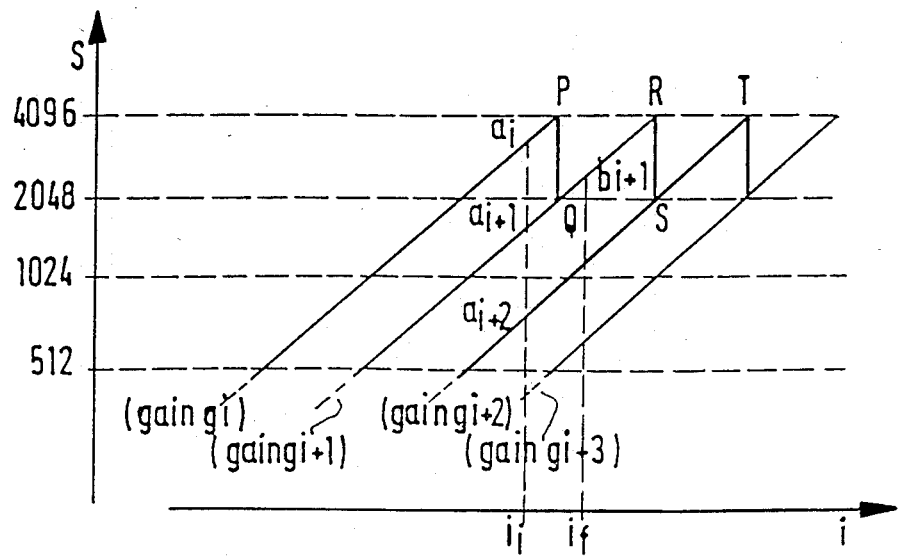
FIG. 6 is a diagram of the variation of the output signals of S as a function of the input signals of i, in the case of the above cited application.

In such an application the main difficulty consists of the measurement of reactions of weak amplitudes, for which the absolute precision required for the ratio $i_f/i_i$ between the signal $i_f$ provided by the detector at the end of the reaction and the signal $i_i$ supplied by the detector at the onset of the reaction must be very good. With the system described above any change in gain occuring the course of the reaction is a source of error, even if the gain ratios are known or were measured previously with the highest possible precision. It is thus necessary to design a method for the selection of gains by the microprocessor which would eliminate the risk of gain changes in the course of the reaction, if said reaction is of a low amplitude and if the direction of the reaction (i increasing or decreasing with time) and the order of magnitude of the amplitude (small or large) of the reaction are not known ahead of time. The difficulty and one mode of resolving it are shown in FIG. 6 which is an enlargement of FIG. 1 within a range of signals chosen as an example.

To illustrate the reasoning, let us consider the case of a reaction translating into the disappearance of a chromogen and thus into an increase in the signal ($i_f < i_i$). Let us assume further that the successive gains are in a very close ratio of 2, which is the case if the LF 13006 circuits of National Semiconductor are used. The minimum acceptable resolution of the measurement is chosen to be of the order of 1/500, which limits the range of the signal i measurable for each gain to a value of S between 512 (limit of acceptable resolution) and 4096 (limit imposed by saturation). Under these conditions the initial value $i_i$ of the signal may in principle be measured on one of three successive gains $g_i$, $g_{i+1}$, $g_{i+2}$, which would yield respectively three values of the signal S: $a_i$, $a_{i+1}$ and $a_{i+2}$. The value $a_i$ measured on the gain $g_i$ provides in principle the best absolute measure of $i_i$, as the resolution at $a_i$ is better than at $a_{a+a}$ and $a_{i+2}$. But if this gain $g_i$ is selected for measuring $i_i$, there is the risk that the final signal $i_f$ will have to be measured on the gain $g_{i+1}$, if the value of $i_f$ is beyond the saturation limit of the gain $g_i$. This may actually occur even with $i_i$ and $i_f$ signals that are very close to each other, if by chance $i_i$ and $i_f$ are located on either side of the level corresponding to the point P and Q. Then the signal $i_f$ would be measured on the gain $g_{i+1}$ and would yield the signal $b_{i+1}$ and the inevitable error due to the change in gain $g_i > g_{i+1}$ would reflect with maximum effect on the measure $b_{i+1}/a_i$ of the ratio of $i_f/i_i$. If, on the other hand, care is taken to choose at the outset the gain $g_{i+1}$, the value of S associated with $i_i$ will be $a_{i+1}$ and no error of change in gain will affect the measure $b_{i+1}/a_{i+1}$ of the $i_f/i_i$ ratio. The case of a reaction translating into a reduction of the signal ($i_f < i_i$) should also be considered; this leads by symmetrical reasoning to a preference of $g_{i+1}$ over $g_{i+2}$ as the initial gain of the measurement of $i_i$. The best choice therefore is to effect the initial measurement on the intermediate gain of the three possible gains, which assures a measurement without the need of a gain change in the course of the reaction for reactions with low amplitudes characterized by $\frac{1}{2} < i_f/i_i < 2$. The choice of this intermediate gain is easily accomplished by the $\mu P$ computer at the instant of the onset of the reaction.

Figure 5:
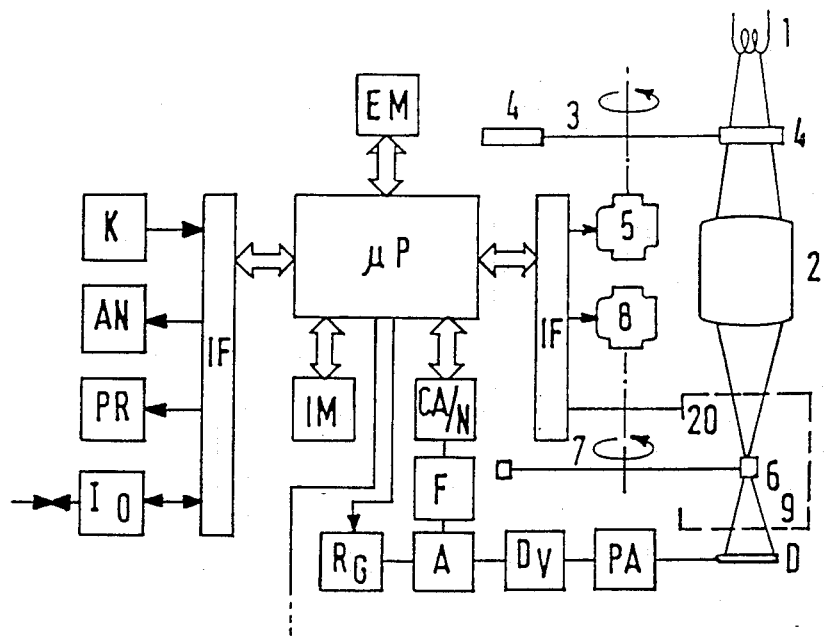
FIG. 5 is a diagram of the application of the assembly to analysis by measuring the transmission of light by a sample.

To illustrate the applications of the devices according to the reaction, reference will be made below to apparatuses wherein a liquid saple is divided between a series of cells, each containing a reagent or a reaction mixture and placed, for example, on the periphery of a rotor to be exposed to the beam of the optical shown in FIG. 5.

The lamp 1 emits a luminous beam toward an optical device 2, with a disk 3 carrying the filters 4 being capable—by means of rotation by a motor 5—of inserting a filter 4 in the path of the beam to insure monochromatism or to completely darken the luminous beam in view of a measurement of black (zero). At the outlet of the optical device 2 the beam is concentrated onto the analytical cell 6 and the unabsorbed light falls onto the detector D followed by the preamplifier PA, the amplifier A and the other elements of FIG. 2.

The cells 6 are mounted on the rotor 7 moved by the motor 8 and the assembly may be placed in a temperature controlled enclosure 9.

The microprocessor $\mu P$ controls the sequence of operations: command to the motor 8 to rotate the rotor 7 and placing the cells 6, rotation command of the motor 5 of the disk 3 and placing of the filters 4 for each cell, performance of the measurements with change of gain if the limit due to saturation or lack of resolution is attained (FIG. 6). The computer $\mu P$ may also select at regular intervals a particular position of the disk 3 with blocks the luminous beam and makes possible the periodical measurement of a black signal intended to correct a possible deviation from zero.

The microprocessor $\mu P$ performs in particular the computation of concentrations from photometric measurements on the basis of the Berr-Lambert law. The molecular extinction coefficients may be stored in a read-only or read-write memory.

The temperature of the enclosure 9 is also controlled by the microprocessor $\mu P$ by means of the thermal probe 10 and one or several sources of temperature correction.

Adequate interfaces are provided between the microprocessor $\mu P$ and the motors 5 and 8, the probe 10 and the temperature control devices.

The microprocessor is in turn connected with an internal memory IM which in part is read-only (logarithmic transformation) and in part read-write (measurements and self-calibration), and with an external read-only memory EM, for example a cassette, card or other EPROM type support containing the indications proper to the type of measurement to be performed (disk 7 and cells 6, disk 3 and filters 4). The microprocessor $\mu P$ is connected with different devices by means of IF interfaces; input keyboard K, alphanumerical display AN, printer PR, input/output I/O connection bus to other equipment.

We claim:

1. An assembly for the conversion of an analog signal into a digital logarithmic signal, comprising:
   a linear amplifier including means for receiving and linearly amplifying an analog signal;
   gain varying means for varying the gain of said linear amplifier;
   an analog-to-digital converter including means for receiving said linearly amplified analog signal from said linear amplifier and converting said linearly amplified analog signal into a digital signal;
   a computer including means for receiving said digital signal and control means for controlling said gain varying means to reduce the gain of said amplifier when the magnitude of said digital signal exceeds a predetermined limit indicative of the saturation point of said analog-to-digital converter, and further including means for converting said digital signal into a digital logarithmic signal according to a predetermined relationship between the logarithm of the digital signal and the gain of said linear amplifier, and wherein the reduction in said gain by said control means is limited to a predetermined value which does not impair the resolution of said analog signal such that, for a particular analog signal, a plurality of adjacent gain levels may be selected by said control means.

2. An assembly as claimed in claim 1, wherein said gain varying means comprises a battery of resistances, each resistance of which is selectable through an electronic gain selection switch controlled by the computer.

3. An assembly as claimed in claim 1, further comprising reference voltage means for supplying a reference voltage to the amplifier upon command by the computer, the output signals from the amplifier resulting from the reference voltage and pairs of possible successive gains, and the ratios of said signals being stored in a memory of the computer as self-calibration, the computer being adapted to make use of said stored signals to perform possible corrections when elaborating the digital logarithmic signal, the reference voltage being disconnected upon command by the computer to return to the analog signal to be converted during the operating phase.

4. An assembly as claimed in claim 3, wherein said reference voltage means comprises a voltage divider receiving the analog signal to be converted and having its output connected to the input of the amplifier, the voltage attenuation of the voltage divider being selectable by the computer during the amplification phases.

5. An assembly as claimed in claim 4, wherein the voltage divider comprises a plurality of electronic switches, each controlled by the computer so that actuation of a given switch by the computer selects a given corresponding voltage attenuation.

6. An assembly as claimed in claim 3, wherein the computer is adapted to initiate said self-calibration prior to each series of signal conversion.

7. An assembly as claimed in claim 3, wherein the computer is adapted to initiate said self-calibration during changes in gain.

8. An assembly as claimed in claim 1, further comprising a low-pass filter electrically connected in series between the amplifier and the analog-to-digital converter.

9. An assembly as claimed in claim 1, further comprising a preamplifier connected to supply said analog signal to said amplifier.

10. An analysis device for analyzing luminous transmission, comprising:
a luminous source adapted to emit a light beam;
an optical system arranged to concentrate the light beam from the source onto at least an analytical cell containing a sample to be analyzed;
a detector receiving the light beam passing through the analytical cell and delivering an analog electrical signal representative of the intensity of said light beam;
and an assembly for the conversion of said analog signal into a digital logarithmic signal, said assembly comprising:
a linear amplifier including means for receiving and linearly amplifying an analog signal;
gain varying mans for varying the gain of said linear amplifier;
an analog-to-digital converter including means for receiving the lineraly receiving the analog signal from said linear amplifier and converting said amplified analog signal into a digital signal;
a computer including means for controlling said gain varying means to reduce the gain of said amplifier when the magnitude of said digital signal exceeds a predetermined limit indicative of the saturation point of said analog-to-digital converter, and further including means for converting of said digital signal into a digital logarithmic signal according to a predetermined relationship between the logarithm of the digital signal and the gain of said linear amplifier, and wherein the reduction in said gain is limited by said control means to a predetermined value which does not impair the resolution of said analog signal such that, for a particular analog signal, a plurality of adjacent gain levels may be selected by said control manes.

11. An analysis device as claimed in claim 10, further comprising a monochromatic filter adapted to be inserted into the luminous path of the light beam from the source.

12. An analysis device as claimed in claim 10, comprising at least two analytical cells adapted to be brought successively into the luminous path of the light beam from the optical system, the first cell containing the sample to be analyzed whereas the second cell contains a reference sample.

13. An analysis device as claimed in claim 10, comprising a series of analytical cells adapted to be brought successively into the path of the light beam from the optical system under the control of the computer.

14. An analysis device as claimed in claim 10, further comprising a series of optical filters arranged to be inserted into the path of the light beam from the source under the control of the computer.

15. An analysis device as claimed in claim 10, further comprising a disc adapted to block the light beam from the source upon a command by the computer.

16. An analysis device as claimed in claim 10, wherein the gain varying means of the amplifier comprises a battery of resistances, each resistance of which is selectable through an electronic gain selection switch controlled by the computer.

17. An analysis device as claimed in claim 10, wherein the conversion assembly further comprises a reference voltage means for supplying a reference voltage to the amplifier upon command by the computer, the output signals from the amplifier resulting from the reference voltage and pairs of possible successive gains, and the ratios of said signals being stored in a memory of the computer as self-calibration, the computer being adapted to make use of said stored signals to perform possible corrections when elaborating the digital logarithmic signal, the reference voltage being disconnected upon command by the computer to return to the analog signal issued from the detector during the operating phase.

18. An analysis device as claimed in claim 17, wherein the reference voltage means of the conversion assembly comprises a voltage divider receiving the analog signal from the detector and having its output connected to the input of the amplifier of said assembly, the voltage attenuation of the voltage divider being selectable by the computer during the amplification phases.

19. An analysis device as claimed in claim 18, wherein the voltage divider of the conversion assembly comprises a plurality of electronic switches, each controlled by the computer so that actuation of a given switch by the computer selects a given corresponding voltage attenuation.

20. An analysis device as claimed in claim 17, wherein the computer of the conversion assembly is adapted to initiate said self-calibration prior to each series of measurements.

21. An analysis device as claimed in claim 17, wherein the computer of the conversion assembly is adapted to initiate said self-calibration during changes in gain.

22. An analysis device as claimed in claim 10, wherein the conversion assembly further comprises a low-pass filter electrically connected in series between the amplifier and the analog-to-digital converter.

23. An analysis device as claimed in claim 10, further comprising a preamplifier adapted to receive the analog signal from the detector and to suppl an analog output signal to the amplifier of the conversion assembly.

24. An analysis device as claimed in claim 18, further comprising a preamplifier amplifier to receive the analog signal from the detector and to suppl an analog output signal to the voltage divider of the conversion assembly.

* * * * *